(12) United States Patent
Fujisawa et al.

(10) Patent No.: US 7,095,012 B2
(45) Date of Patent: Aug. 22, 2006

(54) METHODS AND APPARATUS FOR DETERMINING CHEMICAL COMPOSITION OF RESERVOIR FLUIDS

(75) Inventors: Go Fujisawa, Danbury, CT (US); Oliver C. Mullins, Ridgefield, CT (US); Toru Terabayashi, Sagamihara (JP); Fredrick A. Jenet, Altadena, CA (US); Maria A. van Agthoven, Montrouge (FR); Philip A. Rabbito, Milford, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 297 days.

(21) Appl. No.: 10/450,072

(22) PCT Filed: Dec. 11, 2001

(86) PCT No.: PCT/US01/47731

§ 371 (c)(1),
(2), (4) Date: Nov. 7, 2003

(87) PCT Pub. No.: WO02/066964

PCT Pub. Date: Aug. 29, 2002

(65) Prior Publication Data

US 2004/0069942 A1    Apr. 15, 2004

Related U.S. Application Data

(63) Continuation-in-part of application No. 09/741,575, filed on Dec. 19, 2000, now Pat. No. 6,465,775.

(51) Int. Cl.
*G01V 5/08* (2006.01)
*G01N 21/35* (2006.01)

(52) U.S. Cl. .................... 250/269.1; 250/255

(58) Field of Classification Search ............. 250/269.1, 250/255, 256, 343, 345, 339.13
See application file for complete search history.

(56) References Cited

U.S. PATENT DOCUMENTS

| 3,859,851 | A |   | 1/1975  | Urbanosky ............... 73/155   |
|-----------|---|---|---------|-----------------------------------|
| 4,396,259 | A |   | 8/1983  | Miller .................... 351/158 |
| 4,994,671 | A |   | 2/1991  | Safinya et al. ........... 250/255 |
| 5,161,409 | A | * | 11/1992 | Hughes et al. ......... 73/152.19  |
| 5,167,149 | A |   | 12/1992 | Mullins et al. ........... 73/155  |
| 5,201,220 | A |   | 4/1993  | Mullins et al. ........... 73/155  |
| 5,266,800 | A |   | 11/1993 | Mullins ................ 250/256   |
| 5,331,156 | A |   | 7/1994  | Hines et al. ............ 250/256  |
| 5,360,738 | A | * | 11/1994 | Jones et al. .............. 436/30 |
| 5,557,103 | A | * | 9/1996  | Hughes et al. .......... 250/255   |
| 5,859,430 | A |   | 1/1999  | Mullins et al. .......... 250/255  |

(Continued)

FOREIGN PATENT DOCUMENTS

GB    2 368 391 A    5/2002

OTHER PUBLICATIONS

Badry, Rob et al. *Downhole Optical Analysis of Formation Fluids. Oilfield Review*. (Jan. 1994) pp. 21-28.

(Continued)

*Primary Examiner*—Otilia Gabor
(74) *Attorney, Agent, or Firm*—William B. Batzer; Jody Lynn DeStefanis; William L. Wang

(57) ABSTRACT

Methods of analyzing formation fluids in an oilfield environment are near-infrared absorption spectroscopy. Indications of near-infrared absorptions are analyzed to determine the concentration of compounds in a formation fluid sample.

26 Claims, 9 Drawing Sheets

U.S. PATENT DOCUMENTS

| | | | |
|---|---|---|---|
| 5,939,717 A * | 8/1999 | Mullins | 250/255 |
| 6,274,865 B1 * | 8/2001 | Schroer et al. | 250/269.1 |
| 6,350,986 B1 * | 2/2002 | Mullins et al. | 250/269.1 |
| 6,474,152 B1 * | 11/2002 | Mullins et al. | 73/152.22 |
| 6,956,204 B1 * | 10/2005 | Dong et al. | 250/256 |

OTHER PUBLICATIONS

Crombie, A. et al. *Innovations in Wireline Fluid Sampling. Oilfield Review.* (Autumn 1998) pp. 26-41.

Donahue et al. *Near-Infrared Multicomponent Analysis in the Spectral and Fourier Domains: Energy Content of High-Pressure Natural Gas. Anal. Chem.* (1988), vol. 60, pp. 1873-1878.

Eigenvector Research, Inc. *PLS Toolbox Version 2.1 Handbook* (2000), pp. 75-84.

Ireland, Tim. *The MDT Tool: A Wireline Testing Breakthrough. Oilfield Review.* (Apr. 1992) pp. 58-65.

Malinowski et al. *Factor Analysis in Chemistry* (1980), chap. 2-3.

* cited by examiner

METHODS AND APPARATUS FOR DETERMINING CHEMICAL COMPOSITION OF RESERVOIR FLUIDS

The present application is a continuation-in-part of and claims priority from U.S. application Ser. No. 09/741,575, filed on Dec. 19, 2000, which is incorporated herein by reference in its entirety.

BACKGROUND

Optical analyses of fluids are well known, and various optical and spectroscopic techniques have been applied in oilfield environments to analyze formation fluids, including gases and condensates. For example, U.S. Pat. No. 4,994,671 to Safinya et al. describes an apparatus and method for analyzing the composition of formation fluids. Formation fluids are drawn into a testing region and analyzed by directing light at the fluids and detecting the spectrum of transmitted and/or scattered light. The detected spectra are fit to spectra of known composition to determine the composition of the fluid sample. U.S. Pat. No. 5,266,800 to Mullins and U.S. Pat. No. 5,331,156 to Hines et al. describe applying optical density measurements to distinguish between crude oils and to analyze water and oil fractions, respectively, in, e.g., a formation flow stream obtained by a borehole tool. U.S. Pat. No. 5,167,149 to Mullins et al. and U.S. Pat. No. 5,201,220 to Mullins et al. describe a method and apparatus that involve transmitting light towards a fluid in a flow line and detecting reflected light at various angles of incidence. Information related to the Brewster angle and critical angle of known gas volumes of formation fluids is used to categorize the fluid in the flow line as high gas, medium gas, low gas, and no gas. U.S. Pat. No. 5,859,430 to Mullins et al. describes a borehole tool and method for the downhole analysis of formation gases. When substantial amounts of gas are detected in a fluid stream, the fluid stream is diverted into a sample cell. The gaseous fluid sample is analyzed by directing light to the sample cell and detecting absorbance spectra. The detected spectra are fit to known spectra of various hydrocarbons in order to obtain information regarding the hydrocarbon composition in the gas stream.

U.S. Pat. No. 4,994,671, U.S. Pat. No. 5,266,800, U.S. Pat. No. 5,331,156, U.S. Pat. No. 5,167,149, U.S. Pat. No. 5,201,220, and U.S. Pat. No. 5,859,430 are each incorporated by reference herein in their entireties.

SUMMARY OF INVENTION

The invention provides methods of providing a chemical compositional analysis while sampling a formation fluid in an oilfield environment The method involves extracting a formation fluid sample, transmitting near-infrared light through the formation fluid sample, and detecting indications of near-infrared absorptions from the formation fluid sample. The indications of near-infrared absorptions are analyzed, and the concentrations of a plurality of compounds in the formation fluid sample are determined.

Further details and features of the invention will become more readily apparent from the detailed description that follows.

BRIEF DESCRIPTION OF FIGURES

The invention will be described in more detail below in conjunction with the following Figures, in which.

DETAILED DESCRIPTION

In general, the invention involves the use of near-infrared (NIR) absorption spectroscopy to analyze the chemical composition of a reservoir fluid sample, in some cases in a downhole environment or under downhole conditions. The fraction of light absorbed per unit path length in a fluid sample depends on the composition (i.e., the identity and the concentration, or amount, of the constituent compounds) of the sample and the wavelength of the light Thus, the amount of absorption as a function of wavelength of light, hereinafter referred to as an "absorption spectrum", has been used in the past as an indicator of fluid composition. The present invention extends the use of NIR absorption spectroscopy to provide, in real-time, a more detailed analysis of formation fluids.

Figure 1:
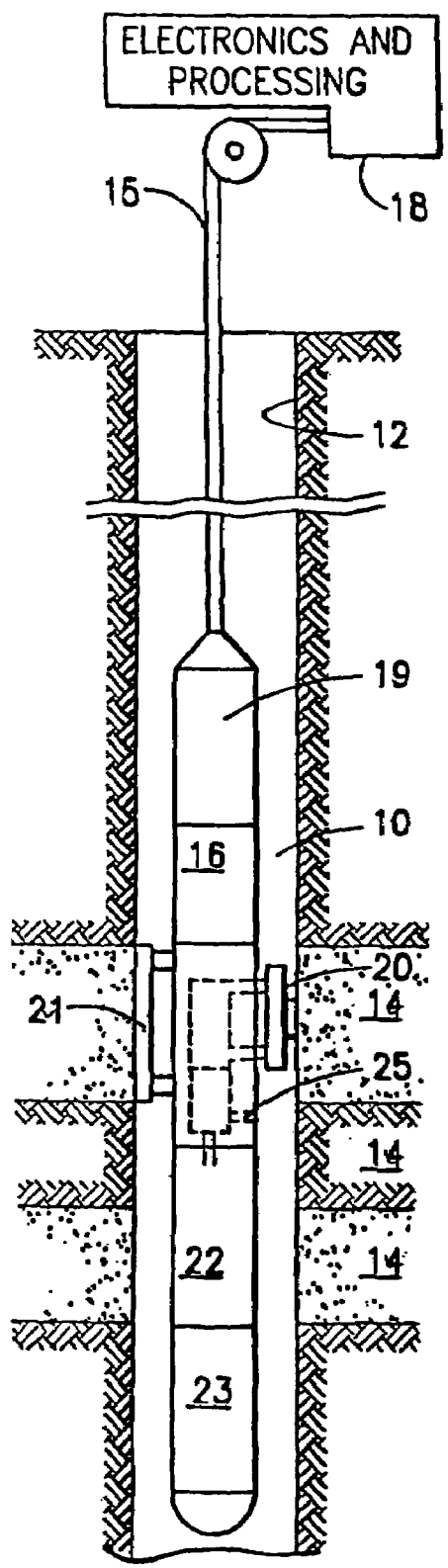
FIG. 1 illustrates a borehole apparatus for analyzing formation fluids that may be used to implement certain embodiments of the invention.

As applied to a downhole environment, the methods of the invention would be implemented using a borehole tool. FIG. 1 illustrates a borehole apparatus that may be used in implementing certain embodiments of the invention. The invention is applicable to both production logging and to borehole investigative logging; some embodiments also are useful for general monitoring of subsurface formations. For purposes of brevity, however, the description herein will be primarily directed to borehole investigative logging, and the terms "borehole" and "borehole tool" should be read throughout the specification and claims to all such environments and evaluation tools used in such environments. Also, the term "sampling" should be read broadly to encompass any sampling of a formation fluid in an oilfield environment, such as from a subsurface formation or a production flow line.

FIG. 1 shows a borehole tool 10 for testing earth formations and analyzing the compositions of fluids from the formation 14 in accord with the invention. As illustrated, the tool 10 is suspended in the borehole 12 from the lower end of a typical multiconductor cable 15 that is spooled in a usual fashion on a suitable winch (not shown) on the formation surface. On the surface, the cable 15 is preferably electrically coupled to an electrical control system 18. The tool 10 includes an elongated body 19 that encloses the downhole portion of the tool control system 16. The elongated body 19 also carries a selectively extendable fluid admitting assembly 20 and a selectively extendable tool-anchoring member 21 that are respectively arranged on opposite sides of the body. The fluid admitting assembly 20 is equipped for selectively sealing off or isolating selected portions of the wall of borehole 12 such that pressure or fluid communication with the adjacent earth formation is established. Also included within the tool 10 is a fluid analysis module 25 through which the obtained fluid flows. The fluid may thereafter be expelled through a port (not shown) or it may be sent to one or more fluid collecting chambers 22 and 23, which may receive and retain the fluids obtained from the formation. Control of the fluid admitting assembly, the fluid analysis section, and the flow path to the collecting chambers is maintained by the electrical control systems 16 and 18.

Additional details of methods and apparatus for sampling formation fluids may be had by reference to U.S. Pat. No. 3,859,851 to Urbanosky and U.S. Pat. No. 4,396,259 to Miller, which are incorporated by reference herein. It should be appreciated, however, that the invention is not intended to be limited to any particular method or apparatus for obtaining the formation fluids.

Figure 2:
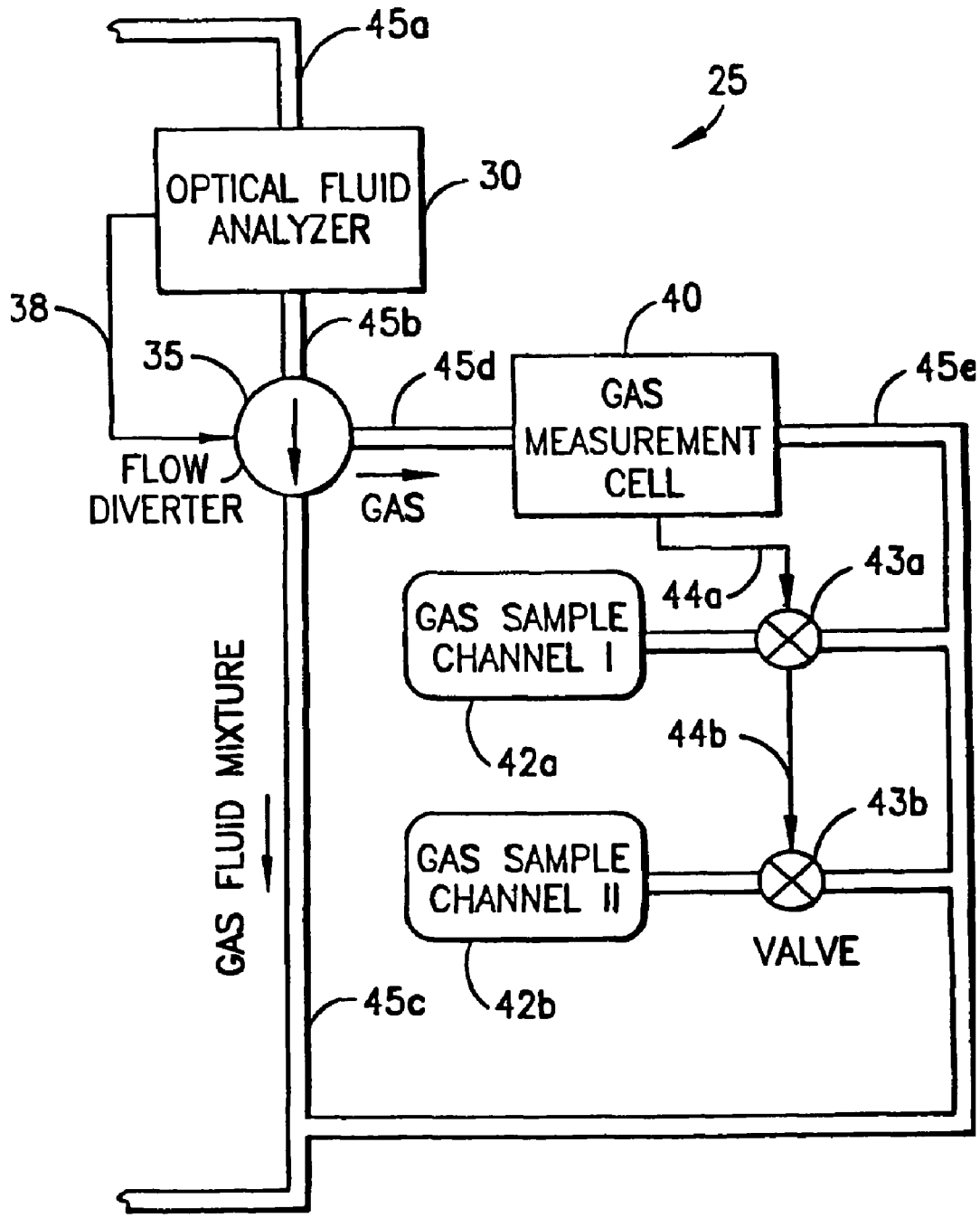
FIG. 2 shows a schematic diagram of a fluid analysis module that can be used in conjunction with a borehole apparatus, such as that shown in FIG. 1, in implementing certain embodiments of the invention.

Turning to FIG. 2, a schematic diagram is seen of one embodiment of a fluid analysis module 25 of FIG. 1. As seen in FIG. 2, the fluid analysis module 25 includes an optical fluid analyzer 30, a flow diverter 35 with associated control line 38, a gas measurement cell 40, optional gas sample chambers 42a and 42b with associated valves 43a, 43b and control lines 44a, 44b, and gas and fluid flow lines 45a, 45b, 45c, 45d, and 45e. The optical fluid analyzer 30, which receives fluids from the borehole and formation via fluid flow line 45a may be an analyzer such as shown and described in previously incorporated U.S. Pat. No. 4,994,671 to Safinya et al., U.S. Pat. No. 5,167,149 to Mullins et al., U.S. Pat. No. 5,201,220 to Mullins et al., U.S. Pat. No. 5,266,800 to Mullins et al., and U.S. Pat. No. 5,331,156 to Hines et al. Thus, the optical fluid analyzer 30 is capable of distinguishing between oil, water, and gas, and as set forth in U.S. Pat. No. 5,167,149 to Mullins et al., and U.S. Pat. No. 5,201,220 to Mullins et al., is capable of categorizing the fluid sample as high gas, medium gas, low gas, and no gas. When the fluid sample contains oil or water, the fluid sample is either optionally stored in sample fluid chambers (not shown), or expelled back into the borehole via fluid flow lines 45b and 45c.

Upon determining that the fluid sample has a high gas content, the fluid analyzer 30 provides a control signal via control line 38 to the flow diverter 35 which diverts the fluid sample via flow line 45d to the gas measurement cell 40 for analysis. While the flow diverter 35 can take many forms, preferably, it is simply embodied as an electronically controlled 2-way valve. After passing through the gas measurement cell 40, the gas may be sent to one or more gas sample chambers 43a, 43b, for storage. Valves 43a, 43b under control of the gas measurement cell 40 via control lines 44a, 44b are provided for that purpose. Alternatively, the gas may be passed via fluid flow line 45e back to fluid flow line 45c for the purpose of being expelled back into the borehole. If desired, backflow or check valves (not shown) may be provided to prevent borehole fluids from backing back into flow line 45d.

Figure 3:
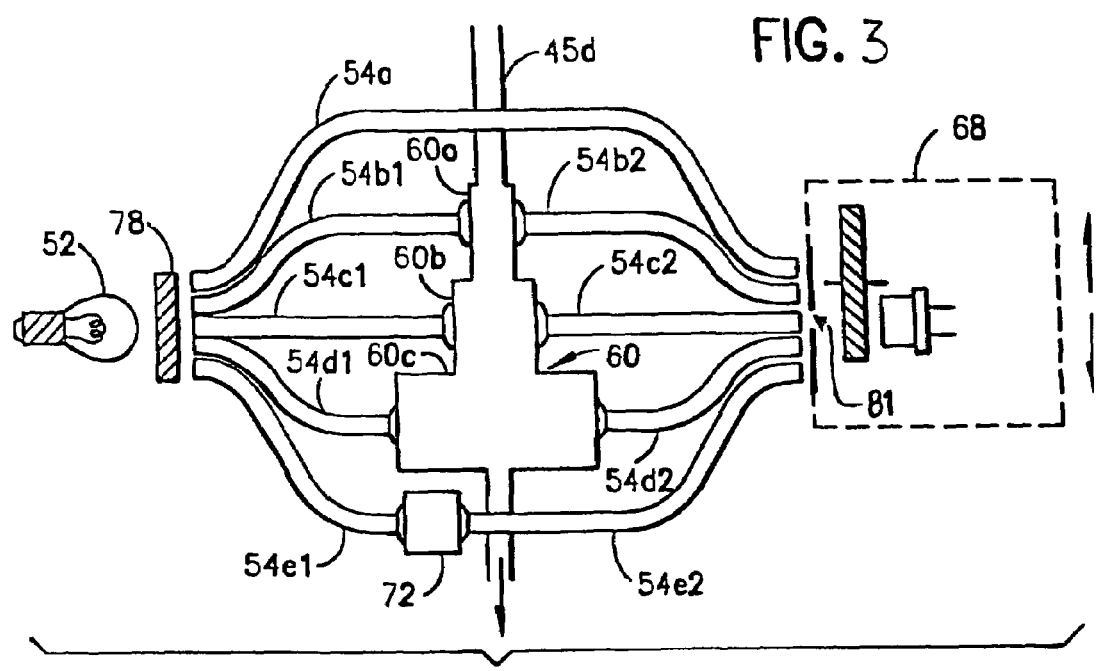
FIG. 3 shows a schematic diagram of one embodiment of a gas measurement cell that can be used in conjunction with a fluid analysis module, such as that shown in FIG. 2.

FIG. 3 shows details of one embodiment of the gas measurement cell 40 which is seen to include a light source 52, a fiber optic bundle(s) 54 (with portions 54a, 54b1, 54b2, 54c1, 54c2, 54d1, 54d2, 54e1 and 54e2), a variable path length vessel 60, including portions 60a, 60b, and 60c, a photo-detector means 68, and a known sample 72. As indicated, gas received via control line 45d is provided to the vessel 60 which includes portion 60a having a 2 mm path length (width), portion 60b having a 4 mm path length, and portion 60c having a 10 mm path length. The vessel 60 includes windows (not shown) through which the light is directed. The light is obtained from the light source 52, which provides light in the near infrared spectrum. The light source 52 may be a narrow bandwidth light emitting diode (LED) or laser, or a broadband source, such as a tungsten halogen lamp, incandescent lamp, or the like, used in conjunction with an optical filter 78 to filter out light of other wavelengths. It should be noted that the light source 52 may reside within the cell within the borehole tool as shown in FIG. 1, or at the surface, with the light from the light source being carried downhole to the cell through optical fibers. Regardless, light from the light source 52 is carried via optical fibers 54b1, 54c1, and 54d1 to the vessel 60, and light emerging from the vessel is carried by optical fibers 54b2, 54c2, and 54d2 to the photo-detector means 68, which may reside within the cell as shown or at the surface. The photo-detector means 68 may include several arrays of photo-detectors tuned to different frequencies of interest, or a single broadband photo-detector with a filter wheel, which permits a time division multiplexed determination of the frequency spectrum of the sample flowing through the vessel. Furthermore, it will be appreciated that, the light emerging from each of the portions 60a, 60b, and 60c may be sensed by different sets of photo-detectors, or as shown in FIG. 3, may be time division multiplexed to a single set of the photo-detectors through an aperture 81 which moves in conjunction with the entire photo-detector means 68. If desired, pressure sensing means may be provided for controlling which optical information is provided to the photo-detectors, as the cell portion having an appropriate path length for sensing the gas and providing a reading in a desired range will often be a function of pressure; i.e., the gas density (and hence absorbance per unit path length) varies as a function of pressure. In any event, it is generally preferable that the light provided to the photo-detector means 68 via fibers 54b2, 54c3, and 54d2 be separately sensed, because where the density of the gas is low, the light emerging from sample portion 60c may provide a desirable signal, but the light emerging from sample portion 60a will be too large and will not permit an appropriate analysis.

As previously mentioned, light from the light source is also carried by fibers 54a for detection by the photo-detector means 68, and by fibers 54e1 to the known reference sample 72, and from the reference sample by fibers 54e2 to the photo-detector means 68. The provision of fibers 54a for carrying light directly to the photo-detector means 68 is known in the art, and is used to cancel drift in the light source, detector, and electronics in order to provide a more robust spectral measurement. The provision of a third path through the known sample 72, however, permits compensation for shifts in actual absorption peak locations or shifts in optical filter wavelengths, yielding an even more robust determination of sample properties in the downhole environment. With the known sample, shifts in detected absorption peak wavelengths or shifts in optical filter wavelengths can be easily determined, thus permitting a relatively straightforward compensation for the unknown sample being analyzed.

Individual absorption peaks may be detected using a broadband light source in conjunction with narrow band filters centered at the selected wavelengths, with the narrow band filters being placed either at the light source, to filter the light before being transmitted through the formation gas, or at the detector, to filter the light after being transmitted through the formation gas. Alternatively, a plurality of narrow band light sources, each producing a narrow band of near-infrared light centered at a selected wavelength, may be used.

Figure 4:
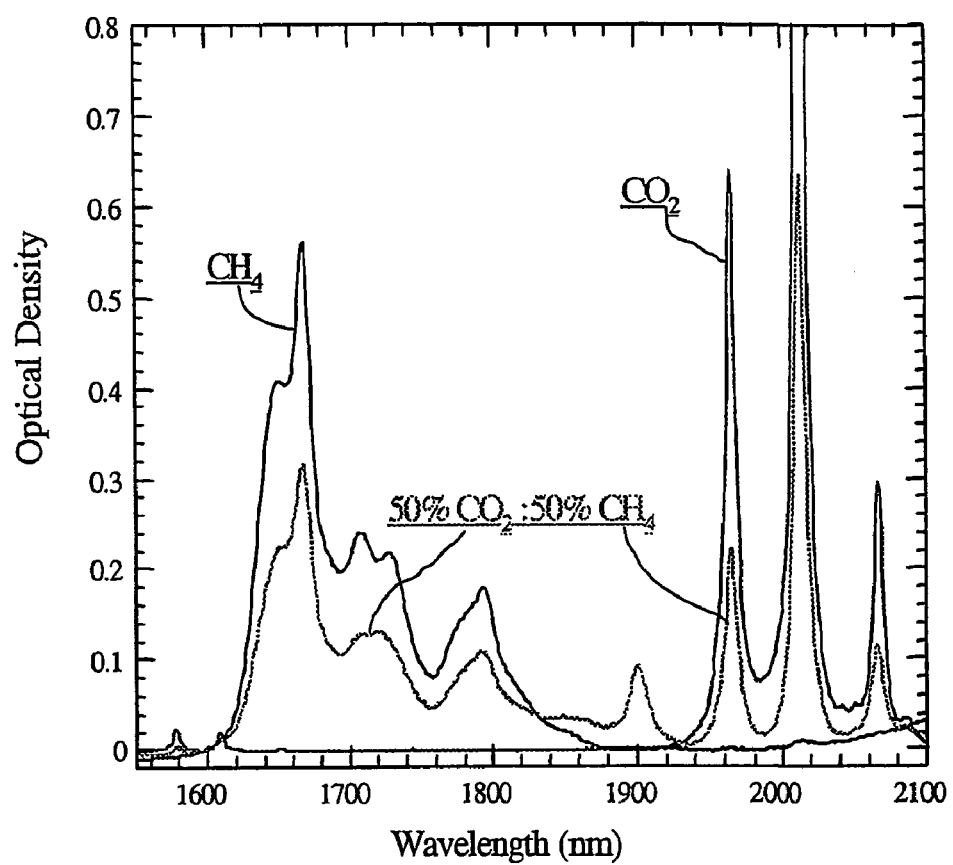
FIG. 4 shows the near-infrared absorption spectra of methane, carbon dioxide, and a 50:50 mixture by mass thereof taken at high pressure.

Other embodiments and additional details of the gas measurement cell 40 are shown and described in previously incorporated U.S. Pat. No. 5,859,430 to Mullins et al. Some embodiments of the present invention use NIR absorption spectroscopy to detect the presence (or absence) of carbon dioxide in downhole environments, or to distinguish carbon dioxide from a hydrocarbon, such as methane, in formation fluids. FIG. 4 shows the near-infrared absorption spectra of methane, carbon dioxide and a 50—50 mass mixture of methane and carbon dioxide from about 1550 nm to about 2100 nm. These absorption spectra show optical density, which is a logarithmic scale measure of the ratio of incident light to light transmitted through the sample, plotted as a function of wavelength. An optical density of zero means that all the incident light at that wavelength is transmitted through the sample and none absorbed, and an optical density of one means that about 90% of the incident light at that wavelength is absorbed.

The absorption spectrum of methane ($CH_4$) shows numerous absorption peaks between about 1600 nm and about 1900 nm, with a large peak at about 1670 nm. The absorption spectrum of carbon dioxide ($CO_2$) shows very little spectral structure in this region and large absorption peaks at about 1960 nm, 2010 nm, and 2060 nm. The absorption spectrum of the 50—50 mixture shows a combination of spectral features of the methane and carbon dioxide spectra, with essentially no alteration of the wavelengths of the absorption peaks resulting from mixing the two gases. The peak at about 1900 nm is believed to be a spurious water absorption; as can be seen from FIG. 4, this spurious peak does not interfere with either the methane or the carbon dioxide absorptions and generally does not affect the optical analyses of the invention discussed below.

The spectra shown in FIG. 4 were taken under about 6000 psi of pressure and at room temperature. While the spectral features of absorption spectra of gases generally vary with temperature and pressure, at pressures above about 1000 psi, the absorption spectra of $CH_4$, $CO_2$, and mixtures thereof lose their ro-vibrational structure and the spectral features lose explicit dependence on temperature and pressure.

Optical density is a function of sample density and hence will vary with pressure for gaseous samples, but varying the path length of the light through the gaseous sample (as discussed above) can help compensate for the effects of pressure on optical density. Thus, the spectra of FIG. 4 indicate that absorption spectra acquired in downhole environments, where pressures can reach 20,000 psi and temperatures can reach over 200° C., can be used to detect carbon dioxide and to distinguish between carbon dioxide and methane.

One embodiment provides methods of detecting the presence (or absence) of carbon dioxide in downhole environments. Carbon dioxide is commonly found, and used, in downhole environments. For example, carbon dioxide may be injected into a subsurface formation to facilitate the flow of oil from the formation to a producing well in an enhanced oil recovery operation, and breakthrough of carbon dioxide into the producing well would be important to detect. In another example, carbon dioxide, a greenhouse gas, may be sequestered in a subsurface formation to remove it from the atmosphere, and carbon dioxide leakage from the subsurface formation would need to be monitored. In such cases, an evaluation tool as described above with respect to FIG. 1, which extracts a sample of formation fluid from the formation into the tool for optical analysis, may be used. Alternatively, an evaluation tool may be injected into a flowing stream of formation fluid, e.g., into the production stream flowing in a production well, and optical analyses performed directly on the flowing stream without drawing the fluid into the tool.

Regardless of whether the evaluation tool extracts a sample of formation fluid from the formation or is injected into a flowing stream of formation fluid, when a gas is detected in the formation fluid (e.g., using the methods described in U.S. Pat. Nos. 5,167,149 and 5,201,220), near-infrared light is transmitted through the formation fluid, and indications of near-infrared absorption are detected from the formation fluid. In one embodiment, the indications of near-infrared absorption are detected over narrow band(s) centered at one or more wavelengths where carbon dioxide is known to absorb. As seen in the spectra of FIG. 4, carbon dioxide has strong absorption peaks at about 1960 nm, about 2010 nm, and about 2060 nm, and the presence (or absence) of carbon dioxide in the formation gas may be detected using any one or more of these known absorption wavelengths. Other known carbon dioxide absorption peaks may be used, though the detection wavelength typically is selected to not overlap with any methane or other formation fluid absorptions. Indications of near-infrared absorption typically also are detected at a wavelength at which neither carbon dioxide nor other formation fluid absorbs in order to determine a baseline from which the carbon dioxide absorption is measured.

Figure 5:
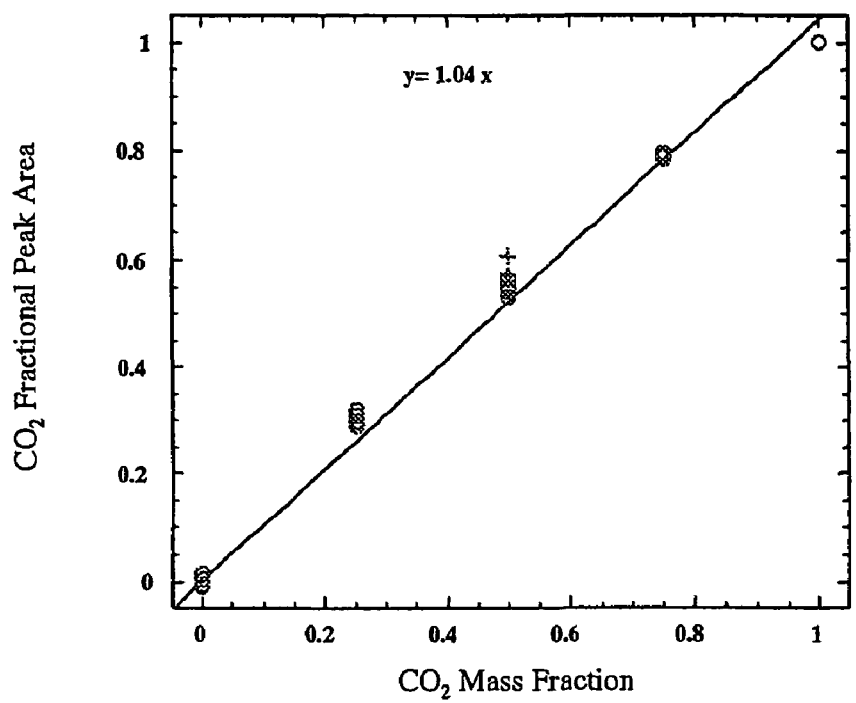
FIG. 5 contains a graph showing a correlation between fractional peak area and carbon dioxide mass fraction in a carbon dioxide-hydrocarbon mixture.

Another embodiment provides a method of distinguishing between carbon dioxide and methane in a downhole environment The presence of carbon dioxide in hydrocarbon production may prove problematic for a number of reasons. When present in natural gas, carbon dioxide reduces the BTU content of the gas, making it less economical to produce. Also, if the gas is brought to the surface, carbon dioxide must be separated from the natural gas, which is a costly procedure. It would be desirable to determine the BTU content of produced gas and to identify and shut off carbon dioxide producing zones before the gas is brought to the surface. This requires a method to distinguish between carbon dioxide and natural gas, which is primarily methane. As described previously, the indications of near-infrared absorptions may be detected at selected wavelengths, as opposed to scanning over a broad range of wavelengths. For example, indications of near-infrared absorption may be detected at about 1960 nm, where carbon dioxide has an absorption peak, and at about 1670 nm, where methane has an absorption peak, though other wavelengths at which carbon dioxide or methane absorbs may be used. To distinguish carbon dioxide and methane, at least three wavelengths typically are used: a first wavelength at which carbon dioxide absorbs; a second wavelength at which methane absorbs; and a third wavelength at which neither carbon dioxide or methane absorbs which is used to determine a baseline from which indications of absorption at the first and second wavelengths are measured. In one embodiment, spectral analysis may be accomplished by comparing the intensities of the detected absorption indications with known absorption spectra from carbon dioxide-methane gas mixtures having different relative mass fractions. The detected absorption indications may be fit to the known spectra using, e.g., a least mean squares fitting, multivariate analysis, etc. In another embodiment, the detected absorption indications may be analyzed in terms of fractional peak areas and correlated with mass fraction using known spectral data. The graph of FIG. 5 illustrates one example of such a correlation. The carbon dioxide fractional peak area was determined as the area of the carbon dioxide peak at about 1960 nm (taken over the full peak width) divided by the sum of peak area of this peak and the methane peak at about 1670 nm (taken over a 25 nm peak width to avoid overlapping with absorption peaks of other hydrocarbons). The carbon dioxide fractional peak area calculated in this fashion shows a nearly 1:1 correlation with carbon dioxide mass fraction in the mixture (the slope of the fitted line equals about 1.04). Thus, detected absorption indications analyzed in this manner provide a direct indication of carbon dioxide mass fraction, and, as indicated above, such correlation appears to be relatively independent of sample pressure and temperature. A linear correlation between methane NIR signal and methane mass fraction also exists, and those of ordinary skill in the art will recognize that this analysis may be applied to determine methane mass fraction. The methods of the invention as applied to detecting carbon dioxide, or distinguishing methane and carbon dioxide, in mixtures of primarily methane and carbon dioxide are relatively straightforward and computationally simple, and may be implemented in the field to provide analytical results in real-time, e.g., while sampling the formation fluid downhole.

These methods also may be extended to measure and analyze NIR spectra of more complex, multi-compound formation fluid mixtures. The inventors have observed that at pressures above about 1000 psi, which is typical of downhole conditions, NIR spectra of even complex formation fluid mixtures lose any explicit dependence on temperature and pressure and depend linearly on compound mass density only. While these observations facilitate the application of the techniques of the present invention to downhole spectra of complex formation fluids, NIR absorption bands of higher hydrocarbons, such as ethane, propane, etc., may overlap with each other and may interfere with the $CO_2$ signal, making simple integration of peak area difficult to implement. Alternatively, such multi-compound formation fluid samples may be analyzed by comparing or fitting the measured NIR absorptions to NIR spectra of known compounds and mixtures, such as in a classical least squares model. This type of analysis, however, typically requires each constituent compound to be known a priori and, as a result, may require a large number of reference spectra to be stored and become time-consuming to implement, making it impractical for real-time, oilfield use. Other types of least squares (e.g., partial least squares, inverted least squares) and multivariate analyses may be used in the methods of the present invention and are described, e.g., in PLS_Toolbox Version 2.1 handbook, Eigenvector Research, Inc., pp. 75–84 (2000) and Donahue et al., "Near-Infrared Multicomponent Analysis in the Spectral and Fourier Domains: Energy Content of High-Pressure Natural Gas", Anal. Chem., 1988, vol. 60, pp. 1873–1878, both of which are incorporated herein in their entireties.

A presently preferred technique applies a principal component regression to the formation fluid NIR spectrum. Principal component regression is a well-known mathematical technique, and has been applied to multi-compound NIR analysis previously. See, e.g., Malinowski and Howery, Factor Analysis in Chemistry (Wiley, New York, 1980), chap. 2–3. However, prior to the present invention, applying principal component regression to downhole spectra of complex formation fluids had not been thought practicable because of the limited spectral data available (typically <10 wavelength channels) from downhole evaluation tools. Embodiments of the present invention provide a way to overcome this obstacle, as will be described below. In order to avoid confusion in the description that follows, the term "compound" shall refer to a chemical species or group in a fluid mixture and the term "component" shall refer to an eigenvector used in the principal component analysis.

Figure 6:
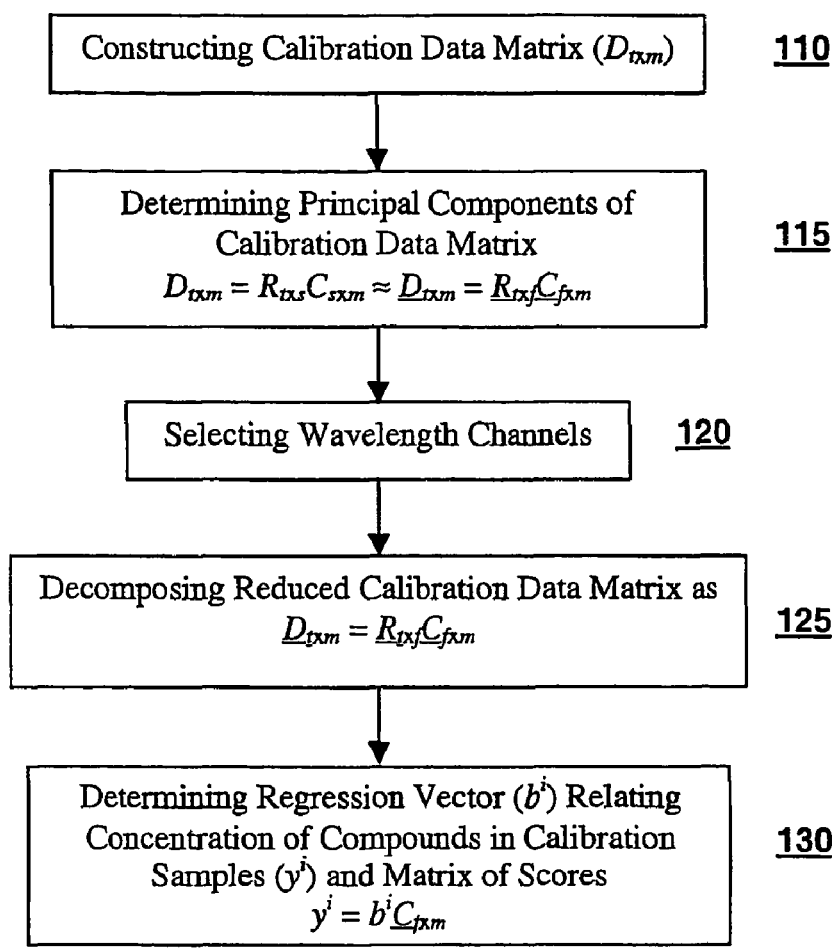
FIG. 6 shows the steps to set up a principal component regression model in accordance with one embodiment of the invention.

Principal component regression reduces the complexity of fitting a multi-compound spectrum to a plurality of reference, or calibration, spectra by analyzing the multi-compound spectrum in terms of the principal components of the calibration spectra. FIG. 6 outlines the steps to set up the principal component regression for field analysis. These steps typically would be completed prior to the actual field measurement and so would not be part of the real-time compositional analysis that occurs in the field.

Beginning at step 110, a calibration data matrix, $D_{t \times m}$, is constructed from a plurality of calibration spectra. The calibration spectra typically include spectra of pure formation fluid compounds as well as known formation fluid mixtures. The calibration data also may include such spectra taken at different temperatures and/or pressures. Each element of the calibration data matrix, $D_{t \times m}$, represents a NIR absorption (e.g., optical density) at one of t wavelengths for one of m calibration samples (e.g., different compound, mixture, temperature, or pressure). To exactly determine the composition of an unknown mixture, at least as many calibration spectra should be used as constituent compounds in the mixture, though less specific information may be determined using fewer calibration spectra Also, over time, as more calibration samples and as actual formation fluid samples are analyzed, those spectra may be added to the calibration data matrix. In general, the more calibration data used, the better the results of the principal component analysis (step 115) and of the ultimate chemical compositional analysis will be. Thus, the calibration data matrix may be quite large, in some cases containing up to several thousand elements.

Figure 7:
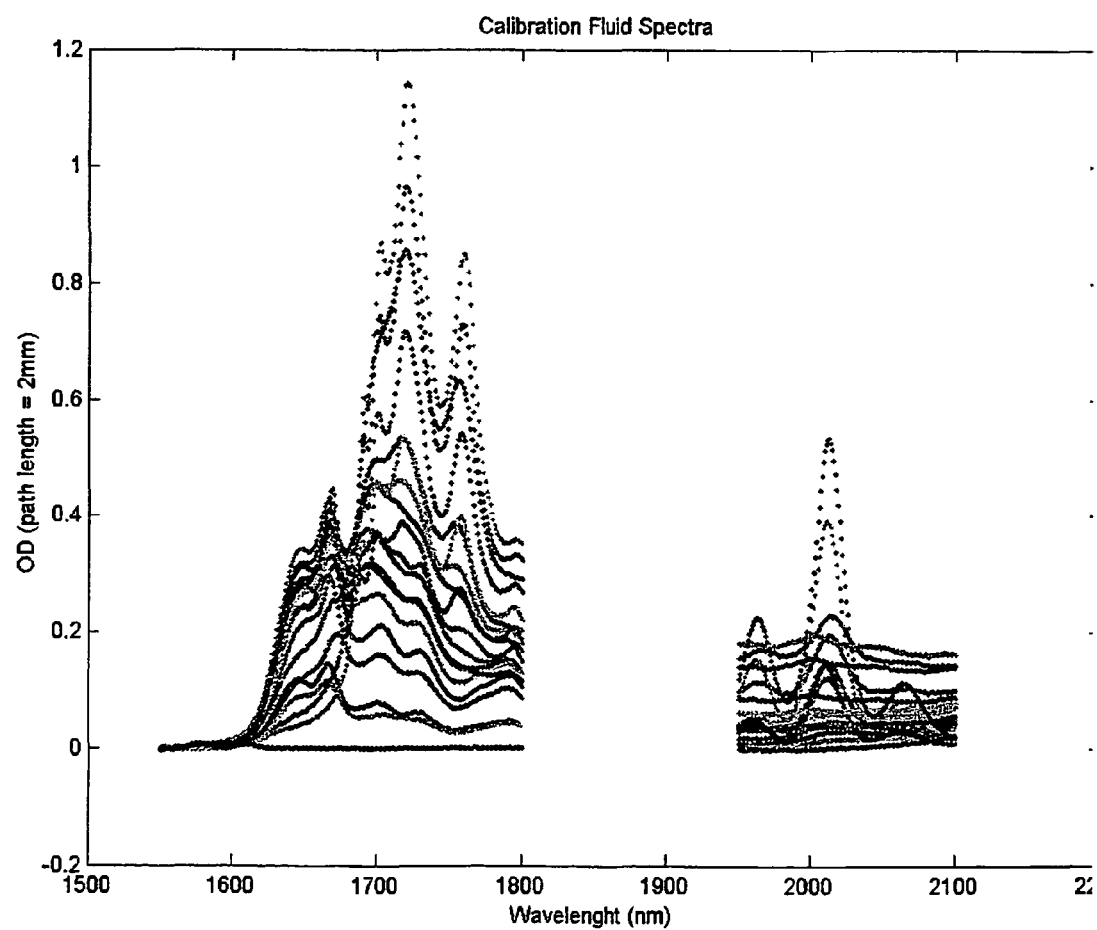
FIG. 7 contains 19 examples of calibration spectra that may be used in some embodiments of the invention.
Figure 8:
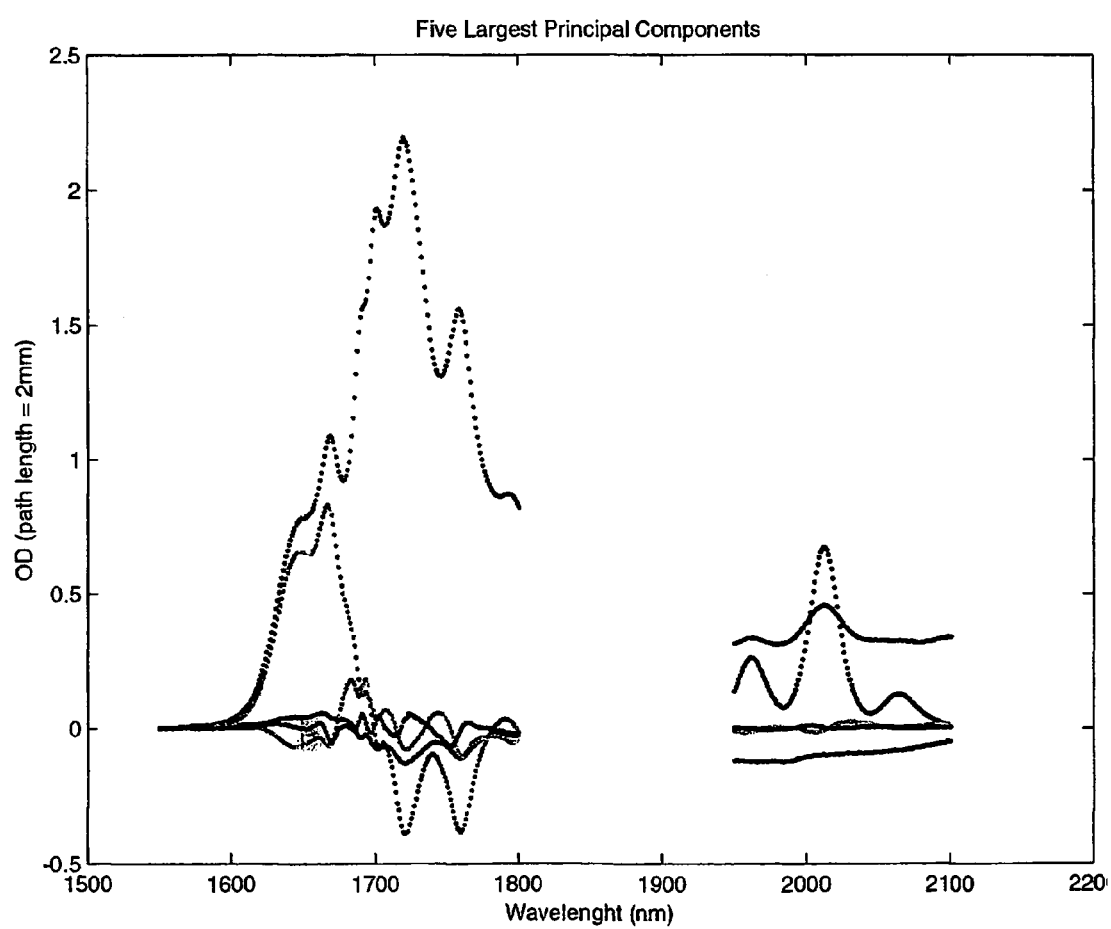
FIG. 8 contains spectra of five principal components of the calibration spectra shown in FIG. 7.

The principal components, or eigenvectors, of the calibration data matrix, $D_{t \times m}$, are determined at step 115 using eigenanalysis, which results in $D_{t \times m}$ being decomposed into two orthogonal matrices, $R_{t \times s} C_{s \times m}$, where s is the smaller of t or m and represents the number of principal components resulting from the eigenanalysis. $R_{t \times s}$ contains the absorptions at the t wavelengths of the s principal components, and $C_{s \times m}$ contains the scores, or weights, of the s components that reproduce the m calibration spectra Some of these s components are associated with experimental errors and may be discarded. For a mixture of n compounds, n components can provide a compositional analysis of all n compounds, assuming the NIR spectrum is a linear mixture of the constituent compound spectra, which is typically the case at high pressure (>about 1000 psi), even for complex formation fluid spectra; more than n components may be used to account for non-linear effects; and fewer than n components may provide useful though less specific information, e.g., about overall trends, or when some constituent compounds have similar spectral features, such as some higher alkanes. In the description that follows, f will be used to designate the number of principal components that are retained for use in the downhole analysis. For f<s, the calibration data matrix may be approximated as $D_{t \times m} \approx \tilde{D}_{t \times m} = R_{t \times f} C_{f \times m}$ FIGS. 7 and 8 help illustrate what happens from step 110 to step 115. FIG. 7 shows the NIR calibration spectra of the 19 fluid samples given in Table 1, below. The NIR spectra shown in FIG. 7 include 400 wavelength channels between approximately 1550 nm and 2100 µm (the region between about 1800 nm and about 1950 nm contains no useful information about hydrocarbon fluids or carbon dioxide and has been discarded here to reduce the possibility of anomalous absorptions interfering with the analysis). In step 110, these calibration spectra would be used to construct the calibration data matrix, $D_{t \times m}$, where, in this case, t=400 and m=19. FIG. 8 shows the spectra of the five largest of the 19 principal components that result from an eigenanalysis of the 19 calibration spectra shown in FIG. 7 (step 115).

Table 1: Composition (in mole %) of Calibration Spectra shown in FIG. 7

| Sample | $CH_4$ | $C_2H_6$ | $C_3$—$C_5$ alkanes | $C_{6+}$ alkanes | $CO_2$ | other ($N_2$) |
|---|---|---|---|---|---|---|
| 1 | 75 | 10 | 15 | 0 | 0 | 0 |
| 2 | 80 | 15 | 5 | 0 | 0 | 0 |
| 3 | 88 | 10 | 2 | 0 | 0 | 0 |
| 4 | 95 | 5 | 0 | 0 | 0 | 0 |
| 5 | 64 | 12 | 4 | 0 | 20 | 0 |
| 6 | 75 | 10 | 5 | 10 | 0 | 0 |
| 7 | 45 | 12 | 8 | 15 | 20 | 0 |
| 8 | 10 | 10 | 10 | 50 | 20 | 0 |
| 9 | 75 | 0 | 0 | 0 | 25 | 0 |
| 10 | 50 | 0 | 0 | 0 | 50 | 0 |
| 11 | 25 | 0 | 0 | 0 | 75 | 0 |
| 12 | 90 | 0 | 0 | 10 | 0 | 0 |
| 13 | 82 | 0 | 0 | 18 | 0 | 0 |
| 14 | 70 | 0 | 0 | 30 | 0 | 0 |
| 15 | 41 | 0 | 0 | 59 | 0 | 0 |
| 16 | 78 | 6 | 7 | 2 | 0 | 7 |
| 17 | 100 | 0 | 0 | 0 | 0 | 0 |
| 18 | 0 | 0 | 0 | 0 | 100 | 0 |
| 19 | 0 | 0 | 0 | 100 | 0 | 0 |

The principle components of the calibration spectra may be used to reconstruct the NIR absorption spectrum of any mixture of the compounds of the calibration samples. As mentioned above, some principal components are associated with experimental errors and may be discarded, though preferably at least as many principal components as constituent compounds to be analyzed for are retained for the analysis. In general, the inventors have found that three to five (f=3-5) principal components are sufficient to analyze a typical formation fluid spectrum in terms of the constituent compounds listed in Table 1; however, other numbers of principal components may be used if desired, for example, to analyze for more constituent compounds, or to account for any non-linear effects.

The calibration data used for $D_{t \times m}$ typically include some spectra generated using laboratory spectrometers, which may have 1000 NIR wavelength channels or more (i.e., t≧1000). A typical downhole optical fluid analyzer, such as described above (see FIGS. 1–3 and accompanying text), however, will have far fewer channels, typically, at present, ≦10, some of which may be reserved for a baseline and/or for other measurements. It had been thought that, with so few wavelength channels, not enough information would be available to apply principal component regression to downhole NIR spectra With the present embodiments, however, the inventors have shown that by selecting wavelength channels at which the variance among the principal components (at least among the f components to be retained for the analysis) is enhanced (step 120), enough information may be captured to successfully apply principal component regression to downhole spectra. Selecting appropriate wavelength channels may be accomplished a number of ways, such as by maximizing some function (e.g., the product) of the eigenvalues of the calibration data matrix, or by looking at the principal component spectra and choosing those wavelengths at which the principal components appear to have the most variance. For example, by looking at the principal component spectra shown in FIG. 8, wavelength bands centered at about 1650 nm, 1690 nm, 1725 nm, 1760 nm, 1960 nm, and 2008 nm appear to capture enough of the relevant information contained in the five principal components and so may be selected for the downhole channels. The number of wavelengths selected (t) will depend on the number of channels available, the calibration data, the number of compounds to be analyzed for, and the number of principal components to be used, and so may include other, or additional, or fewer, wavelengths than those mentioned above. In general, however, at least as many wavelength channels as principal components retained, and preferably more, are used in these embodiments.

Once the wavelength channels for the downhole analyzer are known, a reduced calibration data matrix, $\underline{D}_{t \times m}$, containing only the calibration data for the t wavelength channels, is decomposed into two orthogonal matrices, $\underline{R}_{t \times f} \underline{C}_{f \times m}$ (step 125). $\underline{R}_{t \times f}$ contains the absorptions at the t wavelengths of the f principal components to be used in the downhole analysis, and $\underline{C}_{f \times m}$ contains the scores, or weights, of the f components that approximately reproduce the m calibration spectra.

The final step to set up the principal component regression model for use in the field involves determining a regression or transformation matrix that relates the calibration spectra data and the chemical concentrations of the compounds in the calibration samples (step 130). The modeling to determine this regression or transformation matrix may be based on either Beer's law or inverse Beer's law. Beer's law relates the amount of light a compound absorbs to the concentration of the compound and the distance the light travels through the compound. Inverse Beer's law is a mathematical construct that treats compound concentration as a function of light absorption. While principal component regression based on inverse Beer's law generally provides more stable results and is presently preferred, in some cases, for example, where sufficient calibration data sets (typically >10) are not available, a principal component regression based on (non-inverted) Beer's law may be used. The description that follows is based on inverse Beer's law, but it is to be understood that the present invention encompasses analyses based on either inverse Beer's law or (non-inverted) Beer's law.

Under an inverse Beer's law model, the chemical concentration, $y^i$, of each constituent compound in each calibration sample is related to the scores of the calibration spectra, $\underline{C} f \times m$, by a regression vector, $b^i$:

$$y^i{}_{1 \times m} = b^i{}_{1 \times f} \underline{C}_{f \times m}.$$

Vector $y^i{}_{1 \times m}$ contains the concentrations of the $i^{th}$ constituent compound in the m calibration samples, and vector $b^i{}_{1 \times f}$ contains factors that relate the concentration of the $i^{th}$ constituent compound to the scores of the f principal components. The chemical concentrations in each calibration sample are known, and the scores have been determined previously (in step 125), leaving the regression vector as the only unknown. One straightforward way to determine $b^i$ for each compound is by fitting the concentrations, $y^i$, to the scores, $\underline{C}_{f \times m}$, using a least squares or other known fitting technique. Alternatively, $b^i$ may be determined using inverse matrix techniques, but such methods are more computationally difficult and generally not preferred. Once the regression vector, $b^i$, for each compound and the matrix of principal components, $\underline{R}_{t \times f}$, are known, the principal component regression model is ready to be used in the field.

Figure 9:
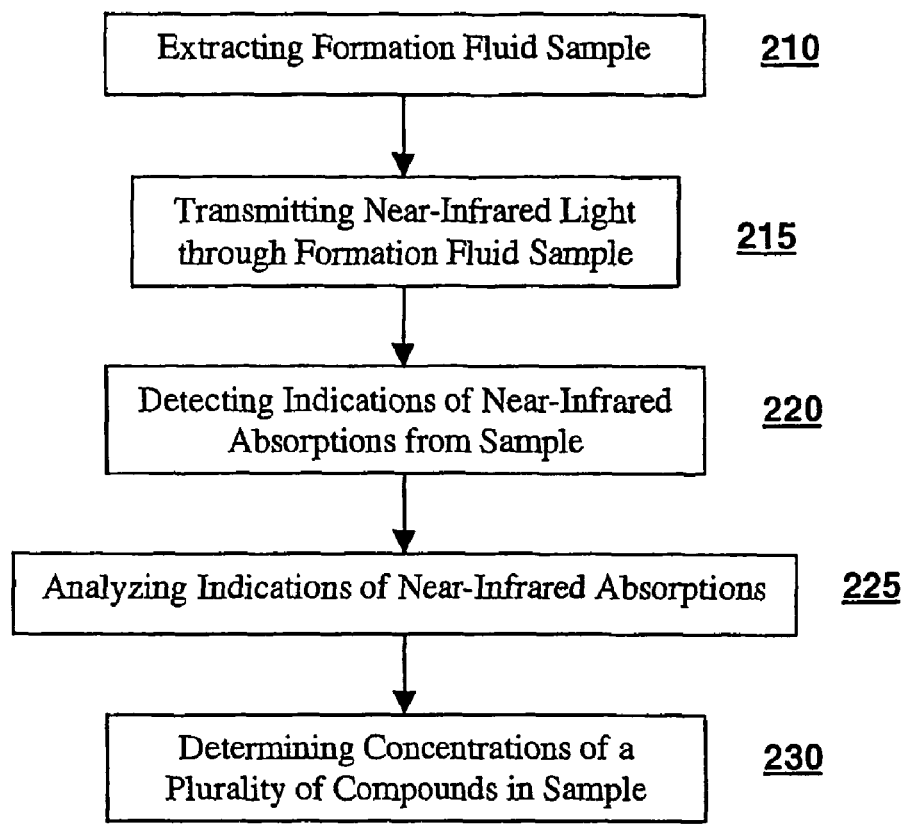
FIG. 9 shows the steps of providing a chemical compositional analysis in an oilfield environment according to one embodiment of the invention.

FIG. 9 outlines the steps according to one embodiment of providing a chemical compositional analysis in an oilfield environment. In step 210, a formation fluid sample is extracted, generally using a borehole tool such as those described previously or from a production flow line. After the sample has been extracted, near-infrared light is transmitted through the formation fluid sample (step 215). Indications of near-infrared absorptions, taken at the pre-determined wavelength channels, are detected from the formation fluid sample at step 220. As described above, these indications may be detected using pluralities of narrow band light sources and detectors, or using a broadband light source, a broadband detector and a plurality of filters, or combinations thereof. The indications of near-infrared absorption are analyzed (step 225), and concentrations of a plurality of compounds, such as methane, carbon dioxide and a higher ($C_{2+}$) hydrocarbon, in the formation fluid sample are determined (step 230).

According to one embodiment, the indications of near-infrared absorptions are analyzed under a principal component regression model. The measured indications of near-infrared absorptions are written as a vector, $M_{t \times 1}$, and multiplied by a pseudo-inverse of $\underline{R}_{t \times f}$ and then by a regression vector, $b^i_{1 \times f}$, to give the concentration, $y^i_{1 \times 1}$, of the $i^{th}$ compound in the formation fluid sample. This process is repeated for each compound to obtain a chemical compositional analysis of the formation fluid sample. In applying the principal component regression model in the field, only information about the plurality of regression vectors, $b^i$, and the matrix of principal components, $\underline{R}_{t \times f}$, need be stored in the processing systems of the tool. These matrices occupy a relatively small amount of memory, especially compared to the plurality of calibration spectra, and may be readily manipulated by most existing borehole tool processing systems, allowing chemical analyses to be made in the field while sampling. There are many ways to determine a pseudo-inverse, such as by multiple linear regression, which expresses the pseudo-inverse of $\underline{R}_{t \times f}$ as $(\underline{R}_{t \times f}^T \underline{R}_{t \times f})^{-1} \underline{R}_{t \times f}^T$. In this case, $y^i$ may be expressed as:

$$y^i_{1 \times 1} = b^i_{1 \times f} (\underline{R}_{t \times f}^T \underline{R}_{t \times f})^{-1} \underline{R}_{t \times f}^T M_{t \times 1}$$

Using this formulation, a principal component regression was applied to the spectra of three known formation fluid mixtures, which were analyzed to determine the concentrations (mole %) of five compounds—methane, ethane, $C_{3-5}$ alkanes, $C_{6+}$ alkanes, and carbon dioxide. Sample 1 resembles a typical dry gas mixture; Sample 2 resembles a typical gas condensate; and Sample 3 resembles a heavier gas condensate with carbon dioxide. The measured spectra were taken at about 100° C. and about 8000 psi pressure to simulate certain downhole conditions using seven wavelength channels ($t=7$). Negative concentration results were set to zero. Table 2 displays the results. The calculated concentrations generally show good agreement with the known values.

TABLE 2

| Known and Calculated Compound Concentrations (mole %) | | | | | |
|---|---|---|---|---|---|
| Sample | $CH_4$ | $C_2H_6$ | $C_{3-5}$ alkanes | $C_{6+}$ alkanes | $CO_2$ |
| 1: known | 88 | 10 | 2 | 0 | 0 |
| calculated | 87 | 9 | 4 | 0 | 0 |
| 2: known | 75 | 10 | 5 | 10 | 0 |
| calculated | 75 | 10 | 7 | 8 | 0 |
| 3: known | 45 | 12 | 8 | 15 | 20 |
| calculated | 43 | 11 | 9 | 12 | 24 |

The invention has been described herein with reference to certain examples and embodiments. It will, however, be evident that various modifications and changes may be made to these embodiments without departing from the scope of the invention as set forth in the claims.

We claim:

1. A method of providing a chemical compositional analysis while sampling a formation fluid in an oilfield environment comprising:
    extracting a formation fluid sample;
    transmitting near-infrared light through the formation fluid sample;
    detecting indications of near-infrared absorptions from the formation fluid sample;
    analyzing the indications of near-infrared light absorptions using a principal component regression model, wherein the principal component regression model is established before sampling the formation fluid in the oilfield environment and establishing the principal component regression model comprises:
        constructing a calibration data matrix from a plurality of near-infrared absorption spectra of calibration samples;
        determining the principal components of the calibration data matrix;
        decomposing the calibration data matrix into a matrix of the principal components and a matrix of scores for the plurality of calibration spectra; and
        determining a plurality of regression vectors, each of which relates concentration of a constituent compound in the calibration samples to the matrix of scores; and
    determining concentrations of a plurality of compounds in the formation fluid sample, the plurality of compounds including: methane and carbon dioxide.

2. The method of claim 1, further comprising:
    introducing a borehole tool into a borehole; and
    using the borehole tool to extract the formation fluid sample into a measurement cell housed within the tool, wherein near-infrared light is transmitted through the measurement cell and indications of near-infrared absorption are detected from the measurement cell.

3. The method of claim 1, wherein the indications of near-infrared absorption are detected from the formation fluid sample at a pressure greater than about 1000 psi.

4. The method of claim 1, wherein the indications of near-infrared absorptions are detected at a plurality of wavelength channels.

5. The method of claim 1, wherein the principal component regression model is based on Beer's law.

6. The method of claim 1, wherein the principal component regression model is based on inverse Beer's law.

7. The method of claim 1, wherein indications of near-infrared absorption are detected at a plurality of wavelength channels.

8. The method of claim 1, wherein the wavelength channels are selected based on the variance among the principal components.

9. The method of claim 1, wherein the plurality of compounds further includes a higher hydrocarbon selected from the group consisting of: ethane, $C_{3-5}$ alkanes, and $C_{6+}$ alkanes.

10. A method of providing a chemical compositional analysis while sampling a formation fluid in an oilfield environment comprising:
   extracting the formation fluid sample;
   transmitting near-infrared light through the formation fluid sample;
   detecting indications of near-infrared absorptions from the formation fluid sample at a plurality of wavelength channels;
   analyzing the indications of near-infrared light absorptions using a principal component regression model, wherein the principal component regression model is established before sampling the formation fluid in the oilfield environment and establishing the principal component regression model comprises:
      constructing a calibration data matrix from a plurality of near-infrared absorption spectra of calibration samples:
      determining the principal components of the calibration data matrix:
      decomposing the calibration data matrix into a matrix of the principal components and a matrix of scores for the plurality of calibration spectra; and
      determining a plurality of regression vectors, each of which relates concentration of a constituent compound in the calibration samples to the matrix of scores; and
   determining concentrations of a plurality of compounds in the formation fluid sample.

11. The method of claim 10, wherein the number of wavelength channels is fewer than 10.

12. The method of claim 10, wherein the indications of near-infrared absorptions are detected using a plurality of filters, each filter transmitting a band of near-infrared light centered at one of the wavelength channels.

13. The method of claim 10, wherein the plurality of wavelength channels is selected based upon the variance among the principal components.

14. The method of claim 10, wherein the principal component regression model is based on Beer's law.

15. The methods of claim 10, wherein the principal component regression model is based on inverse Beer's law.

16. The method of claim 10, wherein determining each regression vector comprises fitting the concentration of the constituent compound to the scores for each of the calibration spectra.

17. The method of claim 10, wherein determining the plurality of regression vectors comprises calculating an inverse matrix of the regression vectors.

18. The method of claim 10, wherein applying the principal component regression model to the indications of near-infrared absorptions comprises calculating a pseudo-inverse of the principal components matrix and applying the pseudo-inverse and then one of the regression vectors to a vector of the indications of near-infrared absorptions.

19. The method of claim 10, wherein the plurality of compounds whose concentrations are determined includes: methane and carbon dioxide.

20. The method of claim 10, wherein the plurality of compounds whose concentrations are determined includes: methane, a higher hydrocarbon, and carbon dioxide.

21. The method of claim 20, wherein the higher hydrocarbon includes: $C_2H_6$, $C_{3-5}$ alkanes, and $C_{6+}$ alkanes.

22. An optical fluid analysis module adapted to be housed within a borehole tool comprising:
   means for transmitting near-infrared light through a formation fluid sample;
   means for detecting indications of near-infrared absorptions from the sample; and
   means for analyzing the indications of near-infrared absorptions to determine concentrations of a plurality of compounds in the sample including methane, carbon dioxide, and a higher hydrocarbon, wherein the means for analyzing the indications of near-infrared absorptions includes a processor and memory means coupled with the processor, the processor being programmed with instructions which, when executed by the processor, cause the processor to apply a principal components regression model to the indications of near-infrared absorptions, wherein the principal component regression model is established before sampling the formation fluid in the oilfield environment and establishing the principal component regression model comprises:
      constructing a calibration data matrix from a plurality of near-infrared absorption spectra of calibration samples;
      determining the principal components of the calibration data matrix;
      decomposing the calibration data matrix into a matrix of the principal components and a matrix of scores for the plurality of calibration spectra; and
      determining a plurality of regression vectors, each of which relates concentration of a constituent compound in the calibration samples to the matrix of scores.

23. The module of claim 22, wherein the means for detecting indications of near-infrared absorptions comprises a detector and a plurality of filters.

24. The module of claim 23, wherein each filter is selected to transmit a band of near-infrared light centered at a pre-selected wavelength.

25. The module of claim 22, wherein the means for detecting indications of near-infrared absorptions comprise a plurality of detectors, each detector being responsive to a band of near-infrared light centered at a pre-selected wavelength.

26. A borehole tool comprising:
   means for extracting a formation fluid sample from a subsurface region into the tool;
      an optical analyzer housed within the tool, the optical analyzer including:
      means for transmitting near-infrared light through the sample,
      means for detecting indications of near-infrared absorptions from the sample, and
      means for analyzing the indications of near-infrared absorptions to determine concentrations of a plurality of compounds in the sample, including methane, carbon dioxide, and at least one higher hydrocarbon, wherein the means for analyzing the indications of near-infrared absorptions includes a processor and memory means coupled with the processor, the processor being programmed with instructions which, when executed by the processor, cause the processor to apply a principal components regression model to the indications of near-infrared absorptions, wherein the principal component regression model is established before sampling the formation fluid in the oilfield environment and establishing the principal component regression model comprises:

constructing a calibration data matrix from a plurality of near-infrared absorption spectra of calibration samples;

determining the principal components of the calibration data matrix:

decomposing the calibration data matrix into a matrix of the principal components and a matrix of scores for the plurality of calibration spectra; and determining a plurality of regression vectors, each of which relates concentration of a constituent compound in the calibration samples to the matrix of scores; and means for diverting the formation fluid sample into the optical analyzer.

* * * * *